(12) United States Patent
Knochel et al.

(10) Patent No.: US 6,348,620 B1
(45) Date of Patent: Feb. 19, 2002

(54) METHOD FOR HOMOGENEOUS ENANTIOSELECTIVE HYDROGENATION USING CATALYTIC FERROCENYL BIS-PHOSPHINE COMPLEXES

(75) Inventors: Paul Knochel; Juan Jose Almena Perea, both of Marburg; Karlheinz Drauz, Freigericht; Ingo Klement, Pohlheim, all of (DE)

(73) Assignee: Degussa-Huls AG, Hanau (DE)

( * ) Notice: Subject to any disclaimer, the term of this patent is extended or adjusted under 35 U.S.C. 154(b) by 0 days.

(21) Appl. No.: 09/335,893

(22) Filed: Jun. 18, 1999

(30) Foreign Application Priority Data

Jun. 19, 1998 (DE) .......................... 198 27 311
Dec. 19, 1998 (DE) .......................... 198 58 866
May 12, 1999 (DE) .......................... 199 21 924

(51) Int. Cl.$^7$ .......................... C07C 69/02; C07F 17/02
(52) U.S. Cl. ...................... 560/231; 556/144
(58) Field of Search .................. 556/144; 560/231

(56) References Cited

FOREIGN PATENT DOCUMENTS

| EP | 0564406 | 10/1993 |
| EP | 0612758 | 8/1994 |
| EP | 0646590 | 4/1995 |

OTHER PUBLICATIONS

Yamamoto et al., Modification of (S)–N, N–Dimethyl–1–[(R)–1', 2–Bis(Diphenylphosphino)–Ferrocenyl]Ethylamine (BPPFA)as a Ligand for Asymmetric Hydrogenation of Olefins Catalyzed By A Chiral Rhodium(I) Complex, The Chemical Society of Japan, pp. 1132–1137, vol. 53, No. 4, Apr. 1980.

Kang et al., Asymmetric Synthesis of a New Cylindrically Chiral and Air–Stable Ferrocenyldiphosphine and its Application to Rhodium–Catalyzed Asymmetric Hydrogenation, Tetrahedron Letters 39 (1998), 5523–5526.

Burk et al., Catalytic Asymmetric Reductive Amination of Ketones Via Highly Enantioselective Hydrogenation of the C=N Double Bond, Tetrahedron, vol. 50, No. 15, pp. 4399–4428, 1994.

*Primary Examiner*—Gary Geist
*Assistant Examiner*—Robert W. Deemie
(74) *Attorney, Agent, or Firm*—Pillsbury Winthrop LLP

(57) ABSTRACT

The present invention is relative to a method for the homogeneous, catalytic, enantioselective hydrogenation of compounds of the general formula (I)

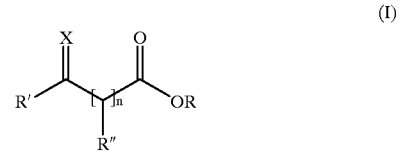

(I)

with the aid of compounds of the general formula (II)

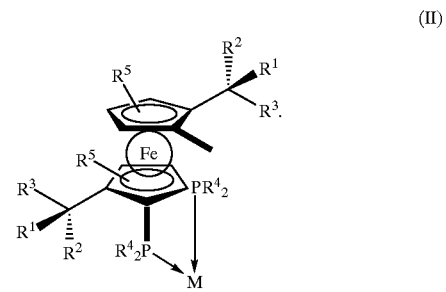

(II)

The use of the hydrogenated derivatives in organic synthesis.

8 Claims, No Drawings

METHOD FOR HOMOGENEOUS ENANTIOSELECTIVE HYDROGENATION USING CATALYTIC FERROCENYL BIS-PHOSPHINE COMPLEXES

CROSS-REFERENCE TO RELATED APPLICATIONS

This application claims priority from German Applications No. 198 27 311.8, filed on Jun. 19, 1998, 198 58 866.6 filed on Dec. 19, 1998 and 199 21 924.9 filed on May 12, 1999, the subject matter of each of which is hereby incorporated herein by reference.

BACKGROUND OF THE INVENTION

1. Field of the Invention

The present invention is relates to a method for the homogeneous, catalytic, enantioselective hydrogenation of compounds of the general formula (I)

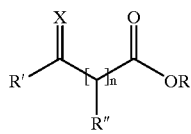

(I)

in which n is a whole number from 0 to 3,

R=H, $(C_1-C_{18})$-alkyl, $(C_6-C_{18})$-aryl, $(C_7-C_{19})$-aralkyl, $(C_3-C_{18})$-heteroaryl, $(C_4-C_{18})$-heteroaralkyl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, or signifies a carboxy protective group, R'=H, $(C_1-C_{18})$-alkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, which groups just cited can be substituted with $(C_1-C_8)$-acyl or $(C_1-C_8)$-alkyloxycarbonyl,

X=O, CHR", NR", NNHR",

R" can be =H, OH, R', $(C_1-C_8)$-alkoxy, $(C_2-C_{18})$-alkoxyalkyl, $(C_1-C_{18})$-acyl, $(C_1-C_{18})$-acyloxy and R" can assume different shapes for different positions in the molecule, or R and R' or R' and R" or R" and R are connected to one another via a $(C_1-C_4)$ bridge which can be singly or multiply substituted with linear or branched $(C_1-C_8)$-alkyl, $(C_1-C_8)$-acyl, $(C_1-C_8)$-alkoxy, $(C_2-C_8)$-alkoxyalkyl groups and/or can contain heteroatoms such as N, O, P, S in the ring, with the aid of $C_2$-symmetric ferrocenyl catalysts.

Furthermore, the invention relates to the use of the derivatives produced by the enantioselective hydrogenation of the invention as chiral intermediates in organic synthesis.

2. Background Information

The enantioselective introduction of stereogenic centers into organic molecules by homogeneously catalyzed hydrogenation is established for special applications on an industrial scale. The enantioselective products are valuable initial substances for the production of bioactive active substances.

The use of bisphosphine catalysts for the enantioselective, homogeneous, catalytic hydrogenation for the purpose just cited is well known (Burk et al., Tetrahedron 1994, 4399).

Knochel et al. (Chem. Eur. J. 1998, 4, 950–968), Hayashi et al. (J. Chem. Soc., Chem Commun. 1989, 495–496), and Ikeda et al. (Tetrahedron Lett. 1996, 4545–4548) describe Pd complexes with $C_2$-symmetric ferrocenyl-(bis-tertiary phosphine) ligands. However, these complexes were used solely in asymmetric allylations. Their use as catalysts in enantioselective hydrogenation was not known up to the present.

Yamamoto at al. (Bull. Chem. Soc. Jpn. 1980, 53, 1132–1137) reported on the use of non $C_2$-symmetric ferrocenyl-(bis-tertiary phosphine) ligands in enantioselective, homogeneous, catalytic hydrogenation. However, good excesses of enantiomers are obtained only very sporadically with these ligands.

DE 19 82 7311.8 and Kang et al. (Tetrahedron Lett. 1998, 39, 5523–5526) disclose $C_2$-symmetric ferrocenyl complexes as suitable catalysts for the enantioselective hydrogenation of acetamido cinnamicacid derivatives.

SUMMARY OF THE INVENTION

It is an object of the present invention to provide a method for the homogeneous, catalytic, enantioselective hydrogenation of further, unsaturated systems with the aid of $C_2$-symmetric ferrocenyl catalysts.

The term "multiple bonds" denotes in the framework of the invention double bonds between a carbon atom and another carbon atom or oxygen atom or nitrogen atom.

This objective is achieved by a method using $C_2$-symmetric ferrocenyl catalysts as described hereinbelow.

As a result of the fact that for the homogeneous, catalytic, enantioselective hydrogenation of compounds of the general formula (I)

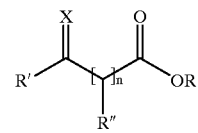

(I)

in which n is a whole number from 0 to 3,

R=H, $(C_1-C_{18})$-alkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, or signifies a carboxy protective group, R'=H, $(C_1-C_{18})$-alkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{19})$-heteroaryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl, which groups just cited can be substituted with $(C_1-C_8)$-acyl or $(C_1-C_8)$-alkyloxycarbonyl,

X=O, CHR", NR", NNHR",

R" can be H, OH, R', $(C_1-C_{18})$-alkoxy, $(C_2-C_{18})$-alkoxyalkyl, $(C_1-C_{18})$-acyl, $(C_1-C_{18})$-acyloxy and R" can assume different shapes for different positions in the molecule, or R and R' or R' and R" or R" and R are connected to one another via a $(C_1-C_4)$ bridge which can be singly or multiply substituted with linear or branched $(C_1-C_8)$-alkyl, $(C_1-C_8)$-acyl, $(C_1-C_8)$-alkoxy, $(C_2-C_8)$-alkoxyalkyl groups and/or can contain heteroatoms such as N, O, P, S in the ring, catalysts of the general formula (II)

(II)

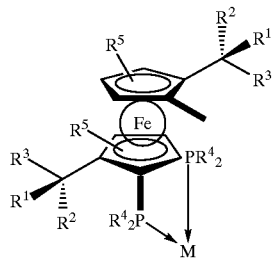

are used
in which
R$^1$, R$^2$ signify, independently of one another, H, NR$^6$R$^7$, SR$^6$,
($C_1$–$C_{18}$)-alkyl, ($C_1$–$C_{18}$)-alkoxy, ($C_2$–$C_{18}$)-alkoxyalkyl, ($C_1$–$C_{18}$)-acyloxy, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl,
($C_1$–$C_8$)-alkyl-($C_6$–$C_{18}$)-aryl,
($C_1$–$C_8$)-alkyl-($C_3$–$C_{19}$)-heteroaryl, ($C_3$–$C_8$)-cycloalkyl,
($C_1$–$C_8$)-alkyl-($C_3$–$C_8$)-cycloalkyl,
($C_3$–$C_8$)-cycloalkyl-($C_1$–$C_8$)-alkyl,
or R$^1$ and R$^2$ are connected via a ($C_3$–$C_7$)-carbocycle which can be singly or multiply substituted with linear or branched ($C_1$–$C_8$)-alkyl, ($C_1$–$C_8$)-acyl, ($C_1$–$C_8$)-alkoxy, ($C_2$–$C_8$)-alkoxyalkyl and/or can contain heteroatoms such as N, O, P, S in the ring,
R$^3$ signifies ($C_2$–$C_{18}$)-alkyl, ($C_1$–$C_{18}$)-alkoxy, ($C_2$–$C_{18}$)-alkoxyalkyl, ($C_1$–$C_{18}$)-acyloxy, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl,
($C_1$–$C_8$)-alkyl-($C_6$–$C_{18}$)-aryl,
($C_1$–$C_8$)-alkyl-($C_3$–$C_{19}$)-heteroaryl, ($C_3$–$C_8$)-cycloalkyl,
($C_1$–$C_8$)-alkyl-($C_3$–$C_8$)-cycloalkyl,
($C_3$–$C_8$)-cycloalkyl-($C_1$–$C_8$)-alkyl,
R$^4$ signifies ($C_1$–$C_{18}$)-alkyl, ($C_6$–$C_{18}$)-aryl, ($C_3$–$C_{18}$)-heteroaryl, ($C_1$–$C_8$)-alkyl-($C_6$–$C_{18}$)-aryl, ($C_1$–$C_8$)-alkyl-($C_3$–$C_{19}$)-heteroaryl, ($C_3$–$C_8$)-cycloalkyl, ($C_1$–$C_8$)-alkyl-($C_3$–$C_8$)-cycloalkyl,
R$^5$ signifies H or a group B-X-Z in which B is a residue selected from the groups CR$^8_2$, NR$^8$, O, S, and SiR$^8_2$, X is a spacer such as, e.g., 1,4'-biphenyl, 1-, 2-ethylene, 1-, 3-propylene, PEG-(2–10) and Z signifies a group bound to a polymer via a functional group such as, e.g., the O—, NH—, COO—, CONH—, ethenyl—, NHCONH—, OCONH— or NHCOO—, or the groups R$^5$ of the two cyclopentadienyl rings are connected to each other via an a, α, ω-($C_2$–$C_4$)-alkylene bridge,
R$^6$, R$^7$ signify, independently of one another, H, ($C_1$–$C_{18}$)-alkyl,
($C_1$–$C_{18}$)-alkoxy, ($C_2$–$C_{18}$)-alkoxyalkyl, ($C_1$–$C_{18}$)-acyl, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl,
($C_1$–$C_8$)-alkyl-($C_3$–$C_{19}$)-heteroaryl, ($C_3$–$C_8$)-cycloalkyl,
($C_1$–$C_8$)-alkyl-($C_3$–$C_8$)-cycloalkyl,
($C_3$–$C_8$)-cycloalkyl-($C_1$–$C_8$)-alkyl,
or R$^6$ and R$^7$ are connected via a ($C_3$–$C_7$)-carbocycle which can be substituted simply or multiply with linear or branched ($C_1$–$C_8$)-alkyl, ($C_1$–$C_8$)-acyl, ($C_1$–$C_8$)-alkoxy, ($C_2$–$C_8$)-alkoxyalkyl and or can contain heteroatoms such as N, O, P, S in the ring,
R$^8$ signifies H, ($C_1$–$C_{18}$)-alkyl and M is a metal atom or metal ion of subgroup 7 or 8 such as, e.g., Co, Ni, Rh, Ru, Ir, Pd, Re or Pt,
the desired hydrogenated derivatives are obtained in a manner which could not have been foreseen in good to very good yields and with good to very good excesses of enantiomers.

Compounds of the general formula (II) are preferably used as catalysts in which
R$^1$, R$^2$ signify, independently of one another, H, N ($C_1$–$C_8$)-alkyl$_2$, NH ($C_1$–$C_8$)-acyl, N ($C_1$–$C_8$)-acyl$_2$, O ($C_1$–$C_8$)-acyl, ($C_1$–$C_8$)-alkyl, ($C_1$–$C_8$)-alkoxy, ($C_2$–$C_8$)-alkoxyalkyl, ($C_3$–$C_7$)-cycloalkyl ($C_6$–$C_{18}$)-aryl,
R$^3$ signifies ($C_3$–$C_7$)-cycloalkyl, ($C_6$–$C_{18}$)-aryl,
R$^4$ signifies ($C_1$–$C_8$)-alkyl, ($C_3$–$C_7$)-cycloalkyl, ($C_6$–$C_{18}$)-aryl,
R$^5$ signifies H.

The use of compounds of general formula (II) as catalysts is quite especially preferred in which
R$^1$, R$^2$ signify, independently of one another, H, O ($C_1$–$C_8$)-acyl, N ($C_1$–$C_8$)-alkyl$_2$, ($C_1$–$C_8$)-alkyl,
R$^3$ signifies ($C_6$–$C_{18}$)-aryl,
R$^4$ signifies phenyl,
R$^5$ signifies H.

The method in accordance with the invention can be carried out in an advantageous manner at a temperature between 0° C. and 150° C., preferably between 20° C. and 80° C.

The hydrogen pressure should be between 10 kPa and 10000 kPa, preferably between 50 kPa and 8000 kPa during the reaction.

All solvents familiar to those skilled in the art can be used as solvents, provided that they do not disturb the result as regards yield and chiral induction. Ethers such as THF, DME, MTBE, alcohols such as MeOH, EtOH, propanol, butanol are preferably used.

The making available of the $C_2$-symmetric catalysts can take place according to DE 19 82 7311.8.

The ferrocenyl catalysts exhibit excellent values during the homogeneous, enantioselective hydrogenation, as shown in Table 1.

TABLE 1

| R | R' | R'' | n | Y | ee value |
|---|----|-----|---|---|----------|
| Et | tBu | — | 0 | Br$_2$ | 95.1% |
| Et | Ph(CH$_2$)$_2$ | — | 0 | Br$_2$ | 71.7% |
| Me | Ph | — | 0 | methylallyl$_2$ | 41.6% |
| H | Ph | — | 0 | methylallyl$_2$ | 31% |

COD stands for 1,5-cyclooctadiene.

The catalytic concentration is already very low, with 1% in the cited examples. However, it can be lowered further for industrial application. Both of these facts are very advantageous for the application of the ligands of the invention on an industrial scale since the expenses for the products obtained according to this method are correspondingly lower and a higher economical use is guaranteed than when using ligand systems of the state of the art.

The $R^5$ group in the complexes can be used, among other things, to bond the complexes of the invention to a polymeric matrix such as, e.g., a linear PMMA, polystyrene or PEG as well as to a non-linear dendrimer. The bonding of the $R^5$ group to the cyclopentadienyl ring of the complex of the invention is variable as regards the free positions and the ring. Therefore, the bonding of the polymer to one ring is sufficient. All groups considered suitable by the skilled artisan for this purpose can be used. A suitable survey for the molecular enlargement of complex catalysts is found in Tetrahedron Asymmetry 1998, 9, 691–696. The $R^5$ group preferably consists of the arrangement B-X-Z in which B is a residue selected from the group $CR^8{}_2$, $NR^8$, O, S, $SiR^8{}_2$, X is a spacer such as, e.g., 1,4'-biphenyl, 1-, 2-ethylene, 1-, 3-propylene, PEG-(2–10) and Z is a functional group such as, e.g., the O—, NH—, COO—, CONH, ethenyl-, NHCONH—, OCONH— or NHCOO— function bound to a polymer like the one described above. Alternatively, the $R^5$ groups of the two cyclopentadienyl rings can be connected to each other via an $\alpha,\omega$-$(C_2$-$C_4)$-alkylene bridge.

The fact that in addition to the acetamido cinnamic-acid derivatives, other unsaturated compounds can be hydrogenated with values which are quite high in some instances, with the $C_2$-symmetric ferrocenyl complexes had not been known previously in the art. It is all the more surprising but not less advantageous that even compounds of type (I) can be reacted enantioselectively.

Methyl, ethyl, n-propyl, isopropyl, n-butyl, isobutyl, sec-butyl, tert-butyl, pentyl, hexyl, heptyl or octyl up to a group comprising 18 C atoms together with all of its bonding isomers can be considered as linear or branched $(C_1$-$C_{18})$-alkyl. The $(C_1$-$C_{18})$-alkoxy group corresponds to the $(C_1$-$C_{18})$-alkyl, provided that the latter is connected to the molecule via an oxygen atom. $(C_2$-$C_{18})$-alkoxyalkyl denotes groups in which the alkyl chain is interrupted by at least one oxygen function and two oxygen atoms are not be connected to one another thereby. The number of carbon atoms indicates the total number of the carbon atoms contained in the group.

The groups just described can be substituted singly or multiply with halogens and/or groups containing N—, O—, P—, S atoms. These are, in particular, alkyl groups of the type cited above which comprise one or several of these heteroatoms in their chain or which are bound to the molecule via one of these heteroatoms. That which was stated above applies correspondingly for the $(C_1$-$C_8)$-alkyl groups for an alkyl group containing at most 8 C atoms.

The term $(C_3$-$C_8)$-cycloalkyl denotes cyclopropyl, cyclobutyl, cyclopentyl, cyclohexyl and cycloheptyl groups, etc. They can be substituted with one or several halogens and/or groups containing, N, O, P, S atoms and/or comprise groups containing N, O, P, S atoms in the ring such as, e.g., 1-, 2-, 3-, 4-piperidyl, 1-, 2-, 3-pyrrolidinyl, 2-, 3-tetrahydrofuryl, 2-, 3-, 4-morpholinyl.

A $(C_3$-$C_8)$-cycloalkyl-$(C_1$-$C_8)$-alkyl group designates a cycloalkyl group as presented above which is bound to the molecule via an alkyl group as indicated above.

$(C_1$-$C_{18})$-acyloxy signifies in the framework of the invention an alkyl group as defined above with a maximum of 18 C atoms which is bound to the molecule via a COO— function. The same applies in a corresponding manner to $(C_1$-$C_8)$-acyloxy.

$(C_1$-$C_{18})$-acyl signifies in the framework of the invention an alkyl group as defined above with a maximum of 18 C atoms which is bound to the molecule via a CO— function. The same applies in a corresponding manner to $(C_1$-$C_8)$-acyl.

$(C_1$-$C_8)$-alkyloxycarbonyl group signifies in the framework of the invention an alkyl group as defined above with a maximum of 8 C atoms which is bound to the molecule via an OCO— function.

The term $(C_6$-$C_{18})$-aryl group denotes an aromatic group with 6 to 18 C atoms. This includes, in particular, compounds such as phenyl groups, naphthyl groups, anthryl groups, phenanthryl groups and biphenyl groups, which can optionally be substituted with $(C_1$-$C_8)$-alkoxy, $NR^6R^7$, $(C_1$-$C_8)$-acyl, $(C_1$-$C_8)$-acyloxy.

A $(C_7$-$C_{19})$- aralkyl group is a $(C_6$-$C_{18})$-aryl group bound to the molecule via a $(C_1$-$C_8)$-alkyl group.

A $(C_3$-$C_{18})$-heteroaryl group designates in the framework of the invention a five- , six- or seven-member, aromatic ring system consisting of 3 to 18 C atoms which comprises heteroatoms such as, e.g., nitrogen, oxygen or sulfur in the ring. Groups such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl are considered in particular as such heteroaromatic compounds.

The term $(C_4$-$C_{19})$-heteroaralkyl denotes a heteroaromatic system corresponding to the $(C_7$-$C_{19})$-aralkyl group.

The term "carboxy protective group" denotes a group as described in J. Jones, The Chemical Synthesis of Peptides, Oxford Science Pub., 1991, p. 33 ff.

Fluorine, chlorine, bromine and iodine can be considered as halogens.

The term "salts" denotes ionic addition compounds of strong acids such as HCl, HBr, $H_2SO_4$, $H_3PO_4$, $CF_3OOH$, p-toluene sulfonic acid, methane sulfonic acid and the molecule under consideration.

PEG signifies polyethylene glycol.

The concept "enantiomer-enriched" denotes in the framework of the invention an amount of an enantiomer in the mixture with its optical antipode in a range of >50% and <100%.

The concept "diastereomer-enriched" denotes the excess of a diastereomer relative to one or several others.

The naming of the complexes and ligands in accordance with the invention comprises in the framework of the invention all possible diastereomers and even the two optical antipodes of a particular diastereomer should be named.

The term "polymers" denotes in the framework of the invention a polymeric matrix such as, e.g., linear PMMA, polystyrene or PEG as well as non-linear dendrimers.

DETAILED DESCRIPTION OF THE INVENTION

The following examples are intended to explain the invention.

EXAMPLES

Hydrogenation of Ketoesters 0.01 mmol Ru $(COD)_2X$ and 0.01 mmol of the ferrocenyl ligand are dissolved in 1 ml acetone under argon in a 25 ml shaker vessel. Then, 0.022 mmol HBr (c=0.3 M; produced from 48% HBr in a suitable amount of MeOH) is added to the solution and the mixture agitated 30 min at RT. The acetone is subsequently distilled off and the residue dissolved in 12 ml of the appropriate solvent. After the addition of 1 mmol of the ketoester the solution is transferred under argon into a 100 ml steel autoclave and heated after multiple rinsing with $H_2$ for 10 min at the appropriate hydrogen pressure to reaction temperature. The mixture is then agitated 24 h, filtered and the enantiomeric excess determined by HPLC.

Trimethylethyl pyruvate [trimethyl pyruvic-acid ethyl ester]

Solvent: EtOH

Reaction temperature: 50° C.

Pressure: 3000 kPa

The conversion was determined by $^1$H-NMR. The enantiomeric excess was determined by HPLC (Chiracel OD, n-heptane/isopropanol 99:1; flow 0.6 mL/min, T=20° C.; $t_R$=10.55 (S), 12.25 (R).

Benzylethyl pyruvate [benzyl pyruvic-acid ethyl ester]

Solvent: EtOH

Reaction temperature: 50° C.

Pressure: 3000 kPa

The conversion was determined by $^1$H-NMR. The enantiomeric excess was determined by HPLC (Chiracel OD, n-heptane/isopropanol 95:5; flow 0.6 mL/min, T=20° C.; $t_R$=14.73 (S), 23.44 (R).

Hydrogenation of Unsaturated Esters/acids 0.01 mmol Ru (COD)$_2$X and 0.01 mmol of the ferrocenyl ligand are dissolved in 12 ml of the appropriate solvent in a 25 ml shaker vessel. After the addition of 1 mmol of the unsaturated ester the solution is transferred under argon into a 100 ml steel autoclave and heated after multiple rinsing with H$_2$ for 10 min. at the appropriate hydrogen pressure to reaction temperature. The mixture is then agitated, filtered, (the optionally added acid esterified with Me$_3$SiCHN$_2$) and the enantiomeric excess determined by HPLC [(Chiracel OJ, n-heptane/isopropanol 95:5; flow 0.6 mL/min, T=20° C.; $t_R$=18.05 (S), 21.13 (R)].

α-phenylacrylic acid:

Solvent: THF

Reaction temperature: 60° C.

Pressure: 5000 kPa

α-phenylmethyl acrylate:

Solvent: MeOH

Reaction temperature: 60° C.

Pressure 5000 kPa

References and patents cited herein are hereby incorporated by reference.

What is claimed is:

1. A method for the homogeneous, catalytic, enantioselective hydrogenation of a compound of formula (I)

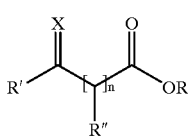

(I)

or R and R' or R' and R" or R" and R are connected to one another via a (C$_1$–C$_4$) bridge which can be singly or multiply substituted with linear or branched (C$_1$–C$_8$)-alkyl, (C$_1$–C$_8$)-acyl, (C$_1$–C$_8$)-alkoxy, (C$_2$–C$_8$)-alkoxyalkyl groups and/or can contain heteroatoms selected from the group consisting of N, O, P, and S in the ring, said method comprising contacting said compound with a catalyst of formula (II)

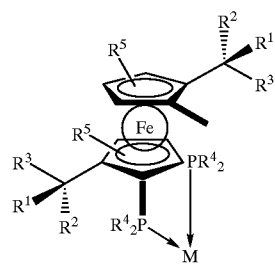

(II)

in which

R$^1$, R$^2$ signify, independently of one another, H, NR$^6$R$^7$, SR$^6$, (C$_1$–C$_{18}$)-alkyl, (C$_1$–C$_{18}$)-alkoxy, (C$_2$–C$_{18}$)-alkoxyalkyl,
(C$_1$–C$_{18}$)-acyloxy, (C$_6$–C$_{18}$)-aryl, (C$_7$–C$_{19}$)-aralkyl,
(C$_3$–C$_{18}$)-heteroaryl, (C$_4$–C$_{19}$)-heteroaralkyl,
(C$_1$–C$_8$)-alkyl-(C$_6$–C$_{18}$)-aryl,
(C$_1$–C$_8$)-alkyl-(C$_3$–C$_{19}$)-heteroaryl, (C$_3$–C$_8$)-cycloalkyl,
(C$_1$–C$_8$)-alkyl-(C$_3$–C$_8$)-cycloalkyl,
(C$_3$–C$_8$)-cycloalkyl-(C$_1$–C$_8$)-alkyl, in which n is a whole number from 0 to 3, R=H, (C$_1$–C$_{18}$)-alkyl, (C$_6$–C$_{18}$)-aryl, (C$_7$–C$_{19}$)-aralkyl,
(C$_3$–C$_{18}$)-heteroaryl, (C$_4$–C$_{19}$)-heteroaralkyl,
(C$_1$–C$_8$)-alkyl-(C$_6$–C$_{18}$)-aryl,
(C$_1$–C$_8$)-alkyl-(C$_3$–C$_{19}$)-heteroaryl, (C$_3$–C$_8$)-cycloalkyl,
(C$_1$–C$_8$)-alkyl-(C$_3$–C$_8$)-cycloalkyl,
(C$_3$–C$_8$)-cycloalkyl-(C$_1$–C$_8$)-alkyl, or signifies a carboxy protective group, R'=H, (C$_1$–C$_{18}$)-alkyl, (C$_6$–C$_{18}$)-aryl, (C$_7$–C$_{19}$)-aralkyl,
(C$_3$–C$_{18}$)-heteroaryl, (C$_4$–C$_{19}$)-heteroaralkyl,
(C$_1$–C$_8$)-alkyl-(C$_6$–C$_{18}$)-aryl,
(C$_1$–C$_8$)-alkyl-(C$_3$–C$_{19}$)-heteroaryl, (C$_3$–C$_8$)-cycloalkyl,
(C$_1$–C$_8$)-alkyl-(C$_3$–C$_8$)-cycloalkyl,
(C$_3$–C$_8$)-cycloalkyl-(C$_1$–C$_8$)-alkyl, which groups just cited can be substituted with (C$_1$–C$_8$)-acyl or (C$_1$–C$_8$)-alkyloxycarbonyl,

X=O, CHR", NR", NNHR",

R" can be =H, OH, R', (C$_1$–C$_{18}$)-alkoxy, (C$_2$–C$_{18}$)-alkoxyalkyl,
(C$_1$–C$_{18}$)-acyl, (C$_1$–C$_{18}$)-acyloxy and R" can assume different shapes for different positions in the molecule, or R$^1$ and R$^2$ are connected via a (C$_3$–C$_7$)-carbocycle which can be singly or multiply substituted with linear or branched (C$_1$–C$_8$)-alkyl, (C$_1$–C$_8$)-acyl, (C$_1$–C$_8$)-alkoxy, (C$_2$–C$_8$)-alkoxyalkyl and/or can contain heteroatoms selected from the group consisting of N, O, P, and S in the ring, R$^3$ signifies (C$_2$–C$_{18}$)-alkyl, (C$_1$–C$_{18}$)-alkoxy,
(C$_2$–C$_{18}$)-alkoxyalkyl, (C$_1$–C$_{18}$)-acyloxy, (C$_6$–C$_{18}$)-aryl,
(C$_7$–C$_{19}$)-aralkyl, (C$_3$–C$_{18}$)-heteroaryl, (C$_4$–C$_{19}$)-heteroaralkyl,
(C$_1$–C$_8$)-alkyl-(C$_6$–C$_{18}$)-aryl,
(C$_1$–C$_8$)-alkyl-(C$_3$–C$_{19}$)-heteroaryl, (C$_3$–C$_8$)-cycloalkyl,
(C$_1$–C$_8$)-alkyl-(C$_3$–C$_8$)-cycloalkyl,
(C$_3$–C$_8$)-cycloalkyl-(C$_1$–C$_8$)-alkyl, R$^4$ signifies (C$_1$–C$_{18}$)-alkyl, (C$_6$–C$_{18}$)-aryl,
(C$_3$–C$_{18}$)-heteroaryl, (C$_1$–C$_8$)-alkyl-(C$_6$–C$_{18}$)-aryl,
(C$_1$–C$_8$)-alkyl-(C$_3$–C$_{19}$)-heteroaryl, (C$_3$–C$_8$)-cycloalkyl, ($C_1$–$C_8$)-alkyl-($C_3$–$C_8$)-cycloalkyl, $R^5$ signifies H or a group B-X-Z in which B is a residue selected from the group consisting of $CR^8{}_2$, $NR^8$, O, S, and $SiR^8{}_2$, X is a spacer selected from the group consisting of 1,4'-biphenyl, 1-, 2-ethylene, 1-, 3-propylene, and PEG-(2–10), and Z signifies a group bound to a polymer via a functional group selected from O—, NH—, COO—, CONH—, ethenyl—, NHCONH—, OCONH— or NHCOO—, or the groups $R^5$ of the two cyclopentadienyl rings are connected to each other via an α, ω-($C_2$–$C_4$)-alkylene bridge, $R^6$, $R^7$ signify, independently of one another, H, ($C_1$–$C_{18}$)-alkyl, ($C_1$–$C_{18}$)-alkoxy, ($C_2$–$C_{18}$)-alkoxyalkyl, ($C_1$–$C_{18}$)-acyl, ($C_6$–$C_{18}$)-aryl, ($C_7$–$C_{19}$)-aralkyl, ($C_3$–$C_{18}$)-heteroaryl, ($C_4$–$C_{19}$)-heteroaralkyl, ($C_1$–$C_8$)-alkyl-($C_6$–$C_{18}$)-aryl, ($C_1$–$C_8$)-alkyl-($C_3$–$C_{19}$)-heteroaryl, ($C_3$–$C_8$)-cycloalkyl, ($C_1$–$C_8$)-alkyl-($C_3$–$C_8$)-cycloalkyl, ($C_3$–$C_8$)-cycloalkyl-($C_1$–$C_8$)-alkyl, or $R^6$ and $R^7$ are connected via a ($C_3$–$C_7$)-carbocycle which may be substituted singly or multiply with linear or branched ($C_1$–$C_8$)-alkyl, ($C_1$–$C_8$)-acyl, ($C_1$–$C_8$)-alkoxy, ($C_2$–$C_8$)-alkoxyalkyl and or can contain heteroatoms selected from the group consisting of N, O, P, and S in the ring, $R^8$ signifies H, ($C_1$–$C_{18}$)-alkyl and M is a metal atom or metal ion of subgroup 7 or 8.

2. The method according to claim 1, wherein a catalyst of formula (II) is used in which $R^1$, $R^2$ signify, independently of one another, H, N ($C_1$–$C_8$)-alkyl$_2$, NH ($C_1$–$C_8$)-acyl, N ($C_1$–$C_8$)-acyl$_2$, O ($C_1$–$C_8$)-acyl, ($C_1$–$C_8$)-alkyl, ($C_1$–$C_8$)-alkoxy, ($C_2$–$C_8$)-alkoxyalkyl, ($C_3$–$C_7$)-cycloalkyl ($C_6$–$C_{18}$)-aryl, $R^3$ signifies ($C_3$–$C_7$)-cycloalkyl, ($C_6$–$C_{18}$)-aryl, $R^4$ signifies ($C_1$–$C_8$)-alkyl, ($C_3$–$C_7$)-cycloalkyl, ($C_6$–$C_{18}$)-aryl, $R^5$ signifies H.

3. The method according to claim 2, wherein $R^1$, $R^2$ signify, independently of one another, H, O ($C_1$–$C_8$)-acyl, N ($C_1$–$C_8$)-alkyl$_2$, ($C_1$–$C_8$)-alkyl, $R^3$ signifies ($C_6$–$C_{18}$)-aryl, $R^4$ signifies phenyl, $R^5$ signifies H.

4. The method according to claim 1 wherein the temperature during the reaction is between 0° C. and 150° C.

5. The method according to claim 4 wherein the temperature is between 20° C. and 80° C.

6. The method according to claim 1, wherein the hydrogen pressure during the reaction is between 10 kPa and 10000 kPa.

7. The method according to claim 6, wherein the pressure is between 50 kPa and 8000 kPa.

8. The method according to claim 1, wherein an ether selected from the group consisting of THF, DME, and MTBE, or an alcohol selected from the group consisting of MeOH, EtOH, propanol, and butanol is used as solvent during the reaction.

* * * * *

UNITED STATES PATENT AND TRADEMARK OFFICE
CERTIFICATE OF CORRECTION

PATENT NO.         : 6,348,620 B1
APPLICATION NO. : 09/335893
DATED                 : February 19, 2002
INVENTOR(S)       : Paul Knochel et al.

It is certified that error appears in the above-identified patent and that said Letters Patent is hereby corrected as shown below:

Title page (57)
The general formula (11), should be deleted and substitute therefore the attached title page.

Column 8 line 1 to 13 the general formula (11) should be deleted and substitute therefore attached page (II).

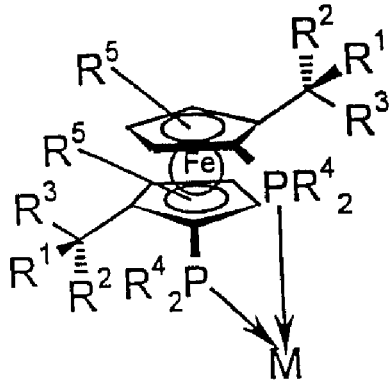

Signed and Sealed this

Fourth Day of March, 2008

JON W. DUDAS
*Director of the United States Patent and Trademark Office*

(12) United States Patent
Knochel et al.

(10) Patent No.: US 6,348,620 B1
(45) Date of Patent: Feb. 19, 2002

(54) METHOD FOR HOMOGENEOUS ENANTIOSELECTIVE HYDROGENATION USING CATALYTIC FERROCENYL BIS-PHOSPHINE COMPLEXES

(75) Inventors: Paul Knochel; Juan Jose Almena Perea, both of Marburg; Karlheinz Drauz, Freigericht; Ingo Klement, Pohlheim, all of (DE)

(73) Assignee: Degussa-Huls AG, Hanau (DE)

(*) Notice: Subject to any disclaimer, the term of this patent is extended or adjusted under 35 U.S.C. 154(b) by 0 days.

(21) Appl. No.: 09/335,893

(22) Filed: Jun. 18, 1999

(30) Foreign Application Priority Data

Jun. 19, 1998 (DE) .................... 198 27 311
Dec. 19, 1998 (DE) .................... 198 58 866
May 12, 1999 (DE) .................... 199 21 924

(51) Int. Cl.⁷ .................... C07C 69/02; C07F 17/02
(52) U.S. Cl. .................... 560/231; 556/144
(58) Field of Search .................... 556/144; 560/231

(56) References Cited

FOREIGN PATENT DOCUMENTS

| EP | 0564406 | 10/1993 |
| EP | 0612758 | 8/1994 |
| EP | 0646590 | 4/1995 |

OTHER PUBLICATIONS

Yamamoto et al., Modification of (S)-N, N-Dimethyl-1-[(R)-1', 2-Bis(Diphenylphosphino)-Ferrocenyl]Ethylamine (BPPFA) as a Ligand for Asymmetric Hydrogenation of Olefins Catalyzed By A Chiral Rhodium(I) Complex, The Chemical Society of Japan, pp. 1132–1137, vol. 53, No. 4, Apr. 1980.

Kang et al., Asymmetric Synthesis of a New Cylindrically Chiral and Air-Stable Ferrocenyldiphosphine and its Application to Rhodium-Catalyzed Asymmetric Hydrogenation, Tetrahedron Letters 39 (1998), 5523–5526.

Burk et al., Catalytic Asymmetric Reductive Amination of Ketones Via Highly Enantioselective Hydrogenation of the C–N Double Bond, Tetrahedron, vol. 50, No. 15, pp. 4399–4428, 1994.

*Primary Examiner*—Gary Geist
*Assistant Examiner*—Robert W. Deemie
(74) *Attorney, Agent, or Firm*—Pillsbury Winthrop LLP

(57) ABSTRACT

The present invention is relative to a method for the homogeneous, catalytic, enantioselective hydrogenation of compounds of the general formula (I)

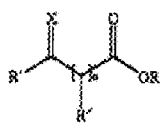

with the aid of compounds of the general formula (II)

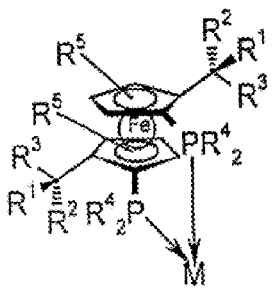

The use of the hydrogenated derivatives in organic synthesis.

8 Claims, No Drawings